(12) United States Patent
Wittmer et al.

(10) Patent No.: US 9,880,038 B2
(45) Date of Patent: Jan. 30, 2018

(54) IN-LINE MEASURING DEVICE

(71) Applicant: Endress + Hauser Conducta GmbH + Co. KG, Gerlingen (DE)

(72) Inventors: Detlev Wittmer, Maulbronn (DE); Manfred Jagiella, Notzingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 16 days.

(21) Appl. No.: 15/063,623

(22) Filed: Mar. 8, 2016

(65) Prior Publication Data

US 2016/0265953 A1 Sep. 15, 2016

(30) Foreign Application Priority Data

Mar. 10, 2015 (DE) .......... 10 2015 103 484

(51) Int. Cl.
*G01F 1/68* (2006.01)
*G01F 9/00* (2006.01)
(Continued)

(52) U.S. Cl.
CPC ............ *G01F 9/001* (2013.01); *G01N 21/00* (2013.01); *G01N 27/4166* (2013.01); *G01F 1/6847* (2013.01); *G01F 1/69* (2013.01)

(58) Field of Classification Search
CPC ................ G01F 1/68; G01F 1/56; G01F 1/37
(Continued)

(56) References Cited

U.S. PATENT DOCUMENTS 6,861,266 B1 3/2005 Sternby
8,479,598 B2 7/2013 Vincent
(Continued)

FOREIGN PATENT DOCUMENTS

CN 2864607 Y 1/2007
CN 101600391 A 12/2009
(Continued)

OTHER PUBLICATIONS

German Search Report, German Patent Office, Munich, DE, dated Sep. 24, 2015.

*Primary Examiner* — Jewel V Thompson
(74) *Attorney, Agent, or Firm* — Christopher R. Powers; PatServe

(57) ABSTRACT

An in-line measuring device for capturing at least two measurands of a measuring medium—especially, a measuring fluid—flowing through a process receptacle, comprising: a first measuring sensor integrated into the process receptacle, with the former being designed to generate a first measuring signal that is dependent upon a flow measurand—especially, a volume and/or mass flow of the measuring medium; a second measuring sensor integrated into the process receptacle, with the former being designed to generate a second measuring signal dependent upon an analysis measurand—especially, one dependent upon the concentration of at least one analyte in the measuring medium and measuring electronics that are connected with the first measuring sensor and the second measuring sensor, with the measuring electronics being designed to receive and process the first measuring signal and the second measuring signal.

22 Claims, 2 Drawing Sheets

(51) Int. Cl.
*G01N 21/00* (2006.01)
*G01N 27/416* (2006.01)
*G01F 1/684* (2006.01)
*G01F 1/69* (2006.01)

(58) Field of Classification Search
USPC .......................... 73/204.11, 861.08, 861.355
See application file for complete search history.

(56) References Cited

U.S. PATENT DOCUMENTS

| | | | | |
|---|---|---|---|---|
| 8,924,165 | B2* | 12/2014 | Kumar | G01F 1/8413 |
| | | | | 702/47 |
| 9,021,878 | B2* | 5/2015 | Grinstein | A61B 5/208 |
| | | | | 73/204.11 |
| 9,372,107 | B2* | 6/2016 | Kirst | G01F 25/0007 |
| 2010/0320095 | A1 | 12/2010 | Galperin | |
| 2011/0161017 | A1 | 6/2011 | Kumar et al. | |

FOREIGN PATENT DOCUMENTS

| | | | |
|---|---|---|---|
| CN | 101720420 | A | 6/2010 |
| CN | 101796386 | A | 8/2010 |
| CN | 202066529 | U | 12/2011 |
| CN | 202195838 | U | 4/2012 |
| CN | 102478416 | A | 5/2012 |
| CN | 102893134 | A | 1/2013 |
| CN | 104034372 | A | 9/2014 |
| CN | 203881388 | U | 10/2014 |
| DE | 69838400 | T2 | 1/2009 |
| WO | 2007049003 | A1 | 5/2007 |
| WO | 2013158515 | A1 | 10/2013 |
| WO | 2014056709 | A1 | 4/2014 |

* cited by examiner

IN-LINE MEASURING DEVICE

TECHNICAL FIELD

The invention concerns an in-line measuring device for capturing at least two measurands of a measuring medium, especially a measuring fluid, flowing through a process receptacle.

BACKGROUND DISCUSSION

In order to determine the composition of measuring mediums such as gases, gas mixtures, or fluids, very diverse analysis sensors are used in process metrology. An analysis sensor generally comprises a measuring sensor that is designed to generate a measuring signal depending upon an analysis measurand, especially one dependent upon a concentration of at least one analyte in the measuring medium, as well as measuring electronics that determine a measured value representing the analyte concentration in the measuring medium on the basis of the measuring signal. An analyte is one substance or several substances, especially solutes, that are contained in the measuring medium and whose concentration in the measuring medium is to be determined and/or monitored by means of the analysis sensor. The measuring electronics may at least partly be integrated into a measuring transducer arranged directly at the measuring point, with the former having a housing with means for display and input, e.g., a screen or input buttons or keys.

Examples of analysis sensors are conductivity sensors, especially conductive or inductive conductivity sensors, density and viscosity sensors, pH sensors, ion-selective electrodes, dissolved oxygen sensors, gas sensors, and photometric sensors that are designed to determine the concentration of a substance present in a photometric measuring path by means of a photometric absorption measurement, especially Raman spectrometers or NIR spectrometers. Analysis sensors, especially those mentioned here, may be designed as in-line measuring devices whose measuring sensor is integrated into a process receptacle in order to capture a measurand of a measuring medium contained in the process receptacle or flowing through the process receptacle. The process receptacle may, for example, be a basin, a fermenter, or a pipeline and/or a pipe system in a process plant.

It becomes obvious in some applications, where analysis sensors are used in flowing process media, that the quality of the measuring values provided by the analysis sensors frequently depends upon the flow characteristics, especially the flow rate of the measuring medium. The flow rate, especially volume or mass flow rate, is to be understood as a volume and/or a mass of a medium that moves through a cross section, especially a cross section of a process receptacle related to the period of time.

In process metrology, flow rate sensors are often used in addition to analysis sensors for process monitoring and control, which are, for example, used as flow monitors (also referred to as flow switches) or are designed as flow rate measuring devices. Flow monitors serve for qualitative flow rate capturing, especially the determination as to whether or not a medium flows through the process receptacle. Flow rate measuring devices furthermore serve to determine a flow rate measuring value for the medium flowing through the process receptacle. The flow rate sensors are usually integrated into the process receptacle as in-line devices like the analysis sensors mentioned above. They are often arranged in a wall of the process receptacle or comprise a measuring tube that can be integrated into the process receptacle. A flow rate sensor, especially of a flow monitor or a flow rate measuring device, is designed to generate a measuring signal that represents the volume flow rate or the mass flow rate of the measuring medium flowing through the process receptacle and/or the measuring tube. Usually, the measuring sensor is connected with measuring electronics that receive the measuring signals generated by the flow rate sensor and determine flow rate measuring values, in the case of a flow rate measuring device, and a qualitative signal representing the presence of a flow, in the case of a flow value. The measuring electronics may be integrated, at least partly, into a measuring transducer for flow rate sensors as well, featuring a housing with means for display and input.

Known measuring principles that are applied in flow rate sensors according to the state of the art are calorimetric or thermal methods, magnetic-inductive methods, Coriolis methods, effective pressure methods, Doppler methods, ultrasonic transit time methods, transit time methods with laser light, whirling and/or vortex methods, or mechanical methods. Please refer to "Durchfluss-Hanbuch, Ein Leitfaden für die Praxis: Messtechniken-Anwendungen-Lösungen" (Flow Rate Manual—A guide for practical use: measuring techniques—applications—solutions), Endress+Hauser Flowtec AG (eds.), 4th edition, Reinach, 2003, for an overview of those methods.

It may be necessary to determine the amount of analyte carried by a flowing measuring medium within a certain period of time, i.e., a so-called analyte load or a flow rate in relation to the flow rate in some applications for the monitoring and control of industrial processes in process plants. It is required for this purpose that the measuring values from various sensors be collated, e.g., an analysis sensor and a flow rate measuring device. In this, the measuring values captured by the measuring electronics of the various sensors must be either read or transferred to a superordinate processing unit—for example, a process control unit. Direct determination of such an analyte load or a check of the measuring value quality is directly at the measuring point, as well as the display by means of a measuring transducer arranged directly on site, is, therefore, frequently not available without complications. Superordinate processing units such as process control units are, furthermore, not always available in smaller process plants.

SUMMARY OF THE INVENTION

It is therefore the objective of this invention to overcome the disadvantages of state-of-the-art technology.

This objective is reached according to the invention by an in-line measuring device to capture at least two measurands as well as a method.

The in-line measuring device according to the invention for capturing at least two measurands of a measuring medium—especially a measuring fluid—flowing through a process receptacle, comprises:
  a first measuring sensor integrated into the process receptacle, with the former being designed to generate a first measuring signal that is dependent upon a flow measurand, especially a volume and/or mass flow of the measuring medium;
  a second measuring sensor integrated into the process receptacle, with the former being designed to generate a second measuring signal dependent upon an analysis measurand, especially one dependent upon the concentration of at least one analyte in the measuring medium, and measuring electronics that are connected with the first measuring sensor and the second measuring sensor, with the measuring electronics being designed to receive and process the first measuring signal and the second measuring signal.

The measuring electronics may be designed to determine a measuring value for the flow rate measurand or a qualitative flow rate value from the first measuring signal, and to determine a measuring value of the analysis measurand from the second measuring signal. In addition, the measuring electronics may be designed to determine further values or quantities on the basis of both values.

The process receptacle may, for example, be a basin, a fermenter, or a pipeline and/or a pipe system in a process plant. The measuring medium found inside the process receptacle may, for example, comprise one or several gases and/or one or several liquids. The measuring sensors integrated into the process receptacle form a measuring point. The measuring electronics are preferably arranged directly at the measuring point. For this purpose, the measuring electronics may, for example, be arranged, at least in part, in a measuring transducer housing firmly connected to the measuring sensor. The measuring electronics may also be, at least in part, arranged in a measuring transducer housing that is separately connected via a cable connection or via short-range radio with one or both measuring sensors. The measuring electronics may comprise input and/or output devices. Input devices may, for example, be switches or keys. Output devices may, for example, include a display that can show measuring values determined by the measuring electronics or other values determined by the measuring electronics.

The first and the second measuring sensor may also advantageously be arranged in a common housing. This has the advantage that only a single housing has to be integrated into the process receptacle wall. Consequently, only one connecting flange and/or one connection armature is required to integrate both measuring sensors into the wall of the process receptacle. This compact structure at the same time ensures that the two measuring signals generated by the measuring sensors refer to characteristics of the measuring medium at the same place.

The measuring electronics may be positioned in the same housing as the first and the second measuring sensor. It is advantageous for the connection of the measuring electronics with a superordinate unit, e.g., via a field bus requiring only a single cable, thus limiting the wiring efforts during the installation of the in-line measuring arrangement into the process receptacle.

Since, in this way, measuring electronics that are directly arranged at the measuring point are connected with measuring sensors arranged at the same measuring point, it is possible to determine values on site and without depending upon a superordinate process control unit, and to have those values incorporate measuring values determined both by means of the flow rate measuring sensor and the analysis measuring sensor. In addition, the in-line measuring device also allows checking the quality of the measuring values of the analysis measurand to be monitored with the measuring values determined by the flow rate measuring sensor.

It is furthermore possible to correct measuring values of the second measuring sensor on the basis of a measuring value from the first measuring sensor, e.g., by utilizing deposited data. In this way, it is possible to determine more precise measuring values for the analysis measurand. For example, a measuring value of the second measuring sensor may be corrected according to a measuring value from the first measuring sensor based upon empirical values saved in the measuring electronics and/or calibrating values. It may, for example, be known for a given application that there is a particularly large measuring error or a measuring deviation in a certain direction for a certain volume or mass flow. In this case, correction parameters or calculation specifications may be saved in the measuring electronics which serve to incorporate such a systematic measuring deviation into the measurement assessment. The measuring electronics may be designed to automatically execute such corrections.

The measuring electronics may be designed to derive a status value from the first or the second measuring signal and to consider this status value when processing the other measuring signal, i.e., the one not used to derive the status value. For example, the status value may be considered in such a way that a measuring value determined from the other measuring signal is classified as valid when the status value is zero, or as not valid when the status value is not zero.

The measuring electronics may, for example, be designed to compare the measuring signal used for deriving the status value or a value derived from this measuring signal, e.g., a measuring value, with at least one reference value. Based on the comparison, the measuring electronics can determine a status value referring to the other measuring sensor, to the measuring signal of the other measuring sensor, or to a measuring value derived from the measuring signal. The reference value may, for example, be set as a threshold value deposited in the measuring electronics. Alternatively, the reference value may be given by means of a saved table or a deposited value chart, e.g., as a saved function.

The status value may, for example, represent a quality of the measuring value (measuring quality, reliability of the measuring value) and/or a status of the process plant and/or a condition of that measuring sensor whose measuring signal is not used for determining the status value.

The measuring electronics may further be designed to output the measuring signal not serving to determine the status value, or to output the measuring value derived from it, together with the determined status value, by means of a display unit, e.g., on the displays mentioned above, and/or output it to a superordinate data processing unit.

If the measuring electronics include a display device, they may be especially designed to output a warning or an alarm, on the basis of the determined status value, on the display device.

The measuring electronics may, for instance, have several reference or threshold values saved that serve to compare the measuring signal serving to determine the status value or a value derived from it. In particular, upper and lower threshold values may be given and deposited. Upper threshold values are advantageously determined in such a way that exceeding the upper threshold value by the measuring signal and/or a value derived therefrom corresponds to a deterioration of the measuring value quality of the measuring value derived from the other measuring signal, i.e., the one not serving to determine the status value. Lower threshold values are correspondingly determined in such a way that, if the lower threshold value is not met by the measuring signal and/or a value derived therefrom, this corresponds to a deterioration of the measuring value quality of the measuring value derived from the other measuring signal. One or more of those upper and/or lower threshold values may be warning threshold values. The measuring electronics may be designed to determine a status value assigned to the warning threshold value in case the value of the measuring signal or the value derived therefrom exceeds or falls below such a warning threshold level and to output this status value, possibly as a warning signal, in addition to the measuring value derived from the other measuring signal.

In the same way, one or several alarm threshold values, especially at least one upper and at least one lower alarm threshold value, may be saved in the measuring electronics. The upper alarm threshold value may be advantageously determined and saved in such a way that exceeding the upper threshold value by the measuring signal serving to determine the status value and/or a value derived therefrom corresponds to a deterioration of the measuring value quality of the measuring value derived from the other measuring signal, i.e., the one not serving to determine the status value, to such an extent it can no longer be tolerated. The lower alarm threshold value may be determined and saved in such a way that the failure of the measuring signal and/or the value derived therefrom to meet the lower threshold value corresponds to a deterioration of the measuring value quality of the measuring value derived from the other measuring signal that can no longer be tolerated, and, thus, that the measuring value is no longer reliable. The measuring electronics may be designed to output an alarm signal in case the value of the measuring signal or the status value derived therefrom exceeds and/or falls below an alarm threshold value.

In an advantageous embodiment, the measuring device includes an energy supply unit that is designed to supply both the first and the second measuring sensor and the measuring electronics with energy.

The measuring electronics may further be designed to derive a value of a quantity depending upon both the flow rate measurand and the analysis measurand using the first and the second measuring signal. This quantity may, for example, be a flow rate related to an analyte in a measuring medium. The quantity, depending upon the flow rate measurand and the analysis measurand, may also be an analyte load that represents the analyte amount passing a point of the process receptacle, together with the flowing measuring medium within a given period of time.

In an advantageous embodiment, the first and the second measuring sensor are integrated into a flow-through fitting that may be connected to the process receptacle in such a way that at least a part of the measuring medium flowing through the process receptacle flows through the flow-through fitting.

The process receptacle may be a pipe system, with the flow-through fitting being designed as a pipeline section, especially as a spool piece or pipe spool, having means for connections at its ends, especially flanges or anchor points that serve to connect it to the pipe system. In this way, it is possible to prefabricate the in-line measuring devices in such a way that the first and second measuring sensors are correctly aligned with each other and calibrated and/or adjusted, or, inasmuch as the first and the second measuring sensor comprise several components that may be aligned with each other, the components of the measuring sensors are correctly aligned, calibrated, and/or adjusted to each other. In this way, the entire in-line measuring arrangement may be prefabricated and adjusted before it is installed into the process plant, especially into the process receptacle. This is particularly advantageous if the first measuring sensor is a measuring sensor working according to an optical measuring principle with a transmitter and a receiver that can be aligned with the transmitter.

The in-line measuring device may therefore be assembled—by the manufacturer, for instance—so that the flow-through fitting with the integrated measuring sensors has only to be inserted into an existing process receptacle, especially a pipe system. Furthermore, calibration and/or adjustment may already be conducted, e.g., by the manufacturer or the plant operator, prior to installation of the flow-through fitting into the process receptacle. During the adjustment, especially the first and the second measuring sensor may be calibrated together and/or be adjusted to one another. The calibration data and/or parameters of a calibrating function determined for the calibration or adjustment may be saved in a memory of the measuring electronics or in a memory arranged inseparably at the fitting or one of the measuring sensors is that can be read by the measuring electronics.

The first measuring sensor may be a flow rate sensor functioning on the basis of a thermal or calorimetric method (heat transfer method), an effective pressure method, a transit time method—especially an ultrasound transit time method—a magnetic-inductive method, a Coriolis method, a whirling or vortex method, or a mechanical method.

The first measuring sensor may be designed as a flow monitor. The measuring sensor designed as a flow monitor may, for example, comprise a measure arrangement that is designed to output a signal qualitatively representing the flow of the measuring medium through the process receptacle as a first measuring signal which especially indicates whether the measuring medium flows through the process receptacle or is stationary. This signal may especially represent whether or not there is a flow in the process receptacle.

The first measuring sensor may alternatively or additionally be designed as a flow rate measuring device comprising a measure arrangement that is designed to output a signal quantitatively representing a flow rate measurand—in particular, a volume or mass flow rate of the measuring medium contained in the process receptacle, especially a signal representing a measuring value for the flow rate measurand as a first measuring signal.

If there is a multiphase fluid present in the process receptacle, the phases might separate, when there is no flow in the process receptacle. In this case, the measuring signal provided by the first measuring sensor is indicative of the process status, e.g. whether the process medium is flowing and/or whether there are one or several phases present. In addition, the measuring signal provided by the first measuring sensor is indicative of the quality of a measuring value determined based on the measuring signal of the second measuring sensor. This is due to the fact, that the various phases of the multiphase fluid have different compositions, so that an analysis measurand measured in different phases or a mixture of the phases, respectively, will yield different measuring values.

The second measuring sensor may especially be a conductivity sensor, in particular an inductive or conductive conductivity sensor. Alternatively, the second measuring sensor can be an oxygen sensor, a pH sensor, or an ion-selective electrode for determining a certain ion concentration. The measuring sensor may also be a density or viscosity sensor. The measuring sensor may, for example, be designed as a rod-like electrochemical or optical sensor, or as an optical sensor that has several components which are arranged at a distance to one another. Such an optical—especially photometric or spectrometric—sensor may comprise one or several sources of radiation and one or several receivers of radiation that are both integrated into the flow-through fitting and aligned with one another in such a way that the radiation emitted from the radiation source meets the radiation receiver after interaction with the measuring medium flowing through the flow-through fitting.

Source of radiation and/or receiver of radiation may also be arranged outside the process receptacle or the flow-through fitting. In this case, the process receptacle or the flow-through fitting preferably features a pipeline section that serves to guide the measuring medium, and in which at least one window is arranged, consisting of a material that is transparent for the measuring radiation emitted by the source of radiation. This window serves to channel a measuring beam emitted by the source of radiation into the measuring medium flowing in the process receptacle and to conduct the measuring beam after interaction with the measuring medium to the radiation receiver. Two windows opposite each other are, preferably, provided, so that the radiation runs on a measuring path from the source of radiation through a first window, the measuring medium, and a second window to the radiation receiver.

If the second measuring sensor is a spectrometric sensor, the sensor may, for example, comprise a Raman spectrometer, an ATR spectrometer, a UV/Vis spectrometer, or an NIR or MIR spectrometer. The second measuring sensor may also be a photometer that comprises one or several light emitting diodes as a source of radiation, or a tunable diode laser, TDL, and one or several photo diodes or a photo diode array as the radiation receiver, or a CCD line and/or a CCD array (CCD: charge-couple device).

The invention also comprises a method for capturing an analysis measurand by means of the in-line measuring device according to one of the embodiments as described above, with the measuring electronics receiving and processing the first measuring signal and the second measuring signal.

The measuring electronics may, for example, determine values into which both the first and the second measuring signal or values derived therefrom, especially measuring values derived from the first and second measuring signal, are included.

In one embodiment of the method, the measuring electronics may determine a measuring value of the analysis measurand by means of the second measuring signal and determine a status value assigned to the measuring value of the analysis measurand on the basis of the first measuring signal.

The measuring electronics may in this method determine the status value on the basis of a comparison of the first or second measuring signal or a value derived therefrom with one or several reference values. As described above, the reference values that are predetermined may be one or several upper and/or lower threshold values, with some being warning threshold values, and others alarm threshold values.

The measuring electronics may output in one variation of the method a warning or alarm signal based upon the first or second measuring signal or the status value, especially on the basis of threshold value comparisons. This may, as described above, be output simultaneously with the current measuring value determined from the measuring signal of the second measuring sensor.

In another embodiment of the method, the measuring electronics may determine a measuring value of the flow rate measurand by means of the first measuring signal and determine a status value assigned to the measuring value of the flow rate measurand on the basis of the second measuring signal.

The measuring electronics may in this method determine the status value on the basis of a comparison of the second measuring signal or a value derived therefrom with one or several reference values. As described above, the reference values that are predetermined may be one or several upper and/or lower threshold values, with some being warning threshold values, and others alarm threshold values.

The measuring electronics may output in one variation of the method a warning or alarm signal based upon the second measuring signal or the status value, especially on the basis of threshold value comparisons. This may, as described above, be output simultaneously with the current measuring value determined from the measuring signal of the first measuring sensor.

The measuring electronics may determine values of a flow rate relating to the analyte on the basis of the first and the second measuring signals, or determine an analyte amount passing a point of the process receptacle with the flowing measuring medium within a given period of time.

BRIEF DESCRIPTION OF THE DRAWINGS

The invention is explained in the following in further detail, on the basis of the exemplary embodiments shown in the figures. They show.

DETAILED DISCUSSION IN CONJUNCTION WITH THE DRAWINGS

Figure 1:
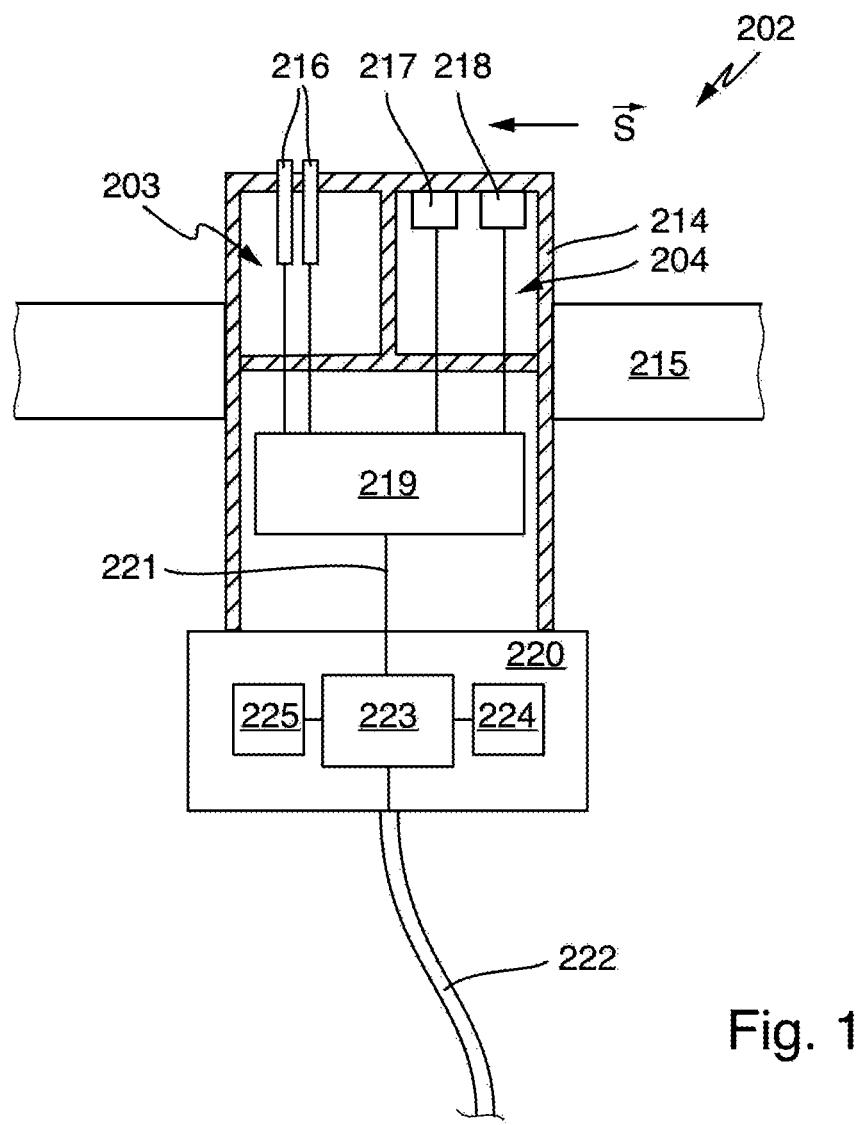
FIG. 1 is a schematic view of a first in-line measure arrangement.

FIG. 1 depicts a schematic view of an in-line measure arrangement 202 combining an analysis sensor, a conductive conductivity sensor—in the present example, and a flow monitor in a single housing. In this embodiment, the in-line measure arrangement 202 has a cylindrical housing 214 that is integrated into a wall 215 of a process receptacle in a process plant. Electrodes 216 are integrated into the front of the housing 214 of a conductive conductivity sensor serving as an analysis measuring sensor 203 contacting a measuring medium flowing through the process receptacle. In a housing chamber that is thermally insulated against the electrodes 216, a heating resistor 218 and a measuring resistor 217 of a flow rate measuring sensor 204 based upon a heat transport method are arranged on the media-contacting front of the housing 214. The measure arrangement of both measuring sensors 203, 204 is arranged on a circuit board 219, also added inside the housing 214. The measure arrangement serves to generate a measuring signal representing the conductivity of the measuring fluid contained in the process receptacle. The measure arrangement further serves to generate a measuring signal that qualitatively represents the flow rate of the measuring medium through the process receptacle. The measure arrangement of the conductivity measuring sensor 203 and the measure arrangement of the flow rate measuring sensor designed as a flow monitor 204 are thus united in a single measure arrangement. Alternatively, the measure arrangements may also be arranged separately on one or several circuit boards.

The measuring signals generated by the measure arrangement are passed on to measuring electronics 223 by one or several connecting lines 221, with the measuring electronics being designed to receive the measuring signals generated by the measuring sensors 203, 204 and process them, and that are arranged in an electronic housing module 220 firmly connected to the housing 214. The measuring electronics 223 may be connected with a superordinate unit via a single cable 222—for example, via a field bus.

The electronic housing module 220 has a display and input keys (not shown in the figure), with the measuring electronics 223 being designed to show values derived from the measuring signals on the display, and to receive and process parameters and commands entered by a user via the input keys and switches.

The measuring electronics 223 are connected with an energy supply unit 224 that supplies the measuring electronics 8 with energy. The measuring electronics may further be designed to supply the measuring sensors 203, 204 with energy.

The in-line measure arrangement 202 is assembled by the manufacturer and needs only to be integrated into an existing process receptacle of a process plant, e.g., into a pipe system. In an alternative embodiment, the measure arrangement 202 may be integrated into a flow-through fitting that has flanges or other connections at both ends, allowing it to be inserted into the process receptacle—especially into a pipeline.

In the present example, the measuring electronics 223 are connected with a radio interface 225 arranged in the electronics housing 220. Via the radio interface 225, the measuring electronics 223 may transfer data, e.g., by short-range radio to a portable control unit such as a smartphone or a tablet PC, and/or receive data from the portable control unit. In this way, a user can configure or set the parameters for the measure arrangement 202 and/or read out measuring values or other values provided by the measuring electronics 223.

The measuring signal of the conductivity sensor serving as analysis measuring sensor 203 may serve for the monitoring of a cleaning process, e.g., a CIP process (CIP=cleaning in place), during which one or several detergents are flushed through the process receptacle. The conductivity sensor helps to determine which detergents are present in the process receptacle at a given time. By means of the flow rate measuring sensor 204 designed as a flow monitor, the measuring electronics 223 can determine whether the measuring medium determined with the conductivity sensor flows through the process receptacle or is stationary. On the basis of the measuring signal provided by the flow monitor and the measuring signal provided by the conductivity sensor, the measuring electronics 223 may monitor proper execution of the CIP process. The measuring signal of the flow monitor that contains the status information as to whether the medium currently found in the process receptacle is flowing or stationary may serve as a status signal for the measuring electronics 223. Based upon this status signal, the measuring electronics 223 may classify the current, i.e., the measuring signal from the conductivity sensor captured simultaneously or in temporal connection with the status signal, as either valid or invalid.

Figure 2:
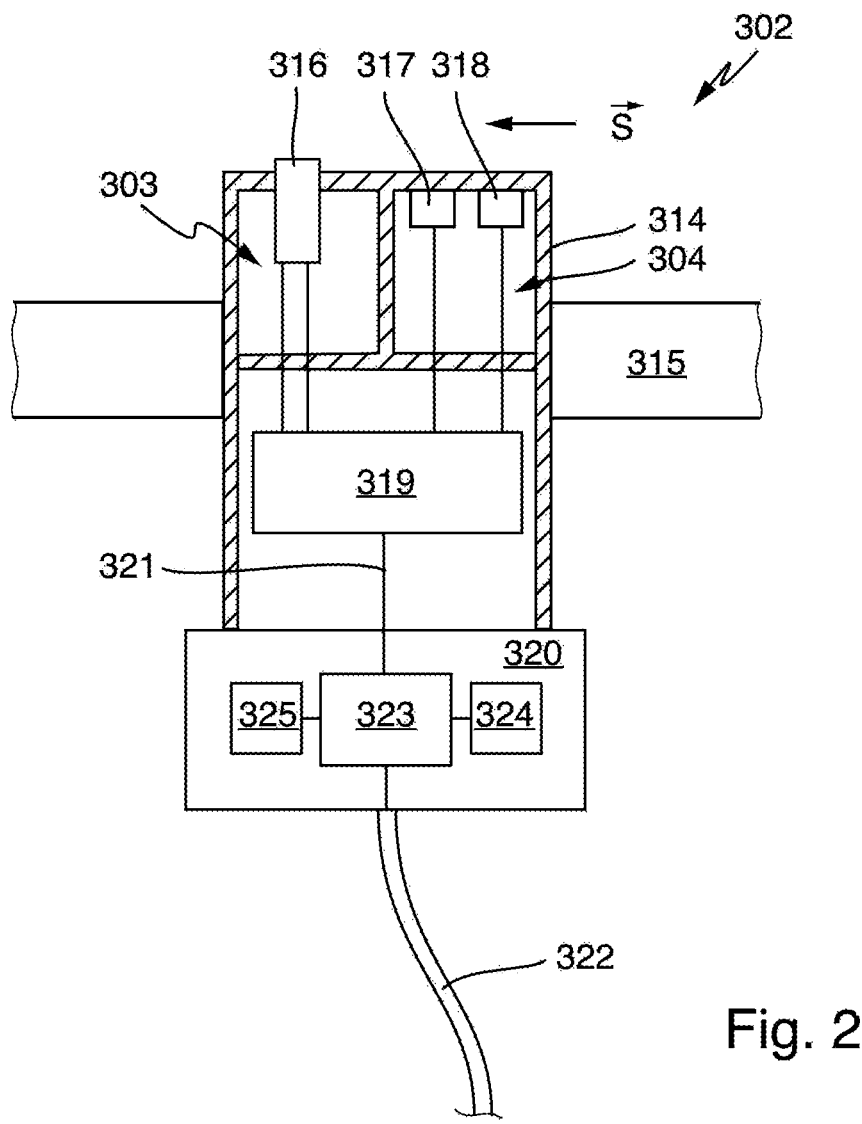
FIG. 2 is a schematic view of a second in-line measure arrangement.

FIG. 2 shows a schematic representation of a second measure arrangement 302 which, in modification of the measure arrangement 202 depicted in FIG. 1, comprises a flow rate measuring sensor 304 that is designed as a flow rate sensor and/or flow rate measuring device. In this embodiment, the measuring sensor has a heat resistor 318 and at least one measuring resistor 317, and the measure arrangement 319 is designed to output a signal quantitatively representing a flow rate measurand, especially a volume or mass flow rate of the measuring medium contained in the process receptacle, in particular, a signal representing a measuring value of the flow rate measurand as a first measuring signal.

The analysis measuring sensor 304 in this example is an amperometric dissolved oxygen sensor 316. It is designed to generate a signal depending upon the concentration of dissolved oxygen in a measuring medium flowing through the process receptacle 315, especially a measuring fluid, and output it to the measure arrangement 319 that generates a second measuring signal dependent upon the concentration of dissolved oxygen.

The two measuring sensors 303, 304, as well as the measure arrangement 319, are arranged in the same housing 314 as in the first example (FIG. 1). In an electronic housing module 320 inseparably connected with this housing 314, there are measuring electronics 323 connected with the measure arrangement 319 that serve for further processing of the first and second measuring signal. The measuring electronics 323 are connected with an energy supply unit 324 that supplies both the measuring electronics and the measuring sensors 303, 304 with energy, like the measuring electronics of the measure arrangement described in FIG. 1. In addition, the measuring electronics 323 are also linked with a radio interface 325 they use to transfer the measuring signal or values derived therefrom to an operating device and/or which can receive data from the operating device. In addition, the electronic housing module 320 may comprise input and output means, e.g., a display and switches. The measuring electronics are connected with a superordinate unit via a cable 322—for example, via a field bus.

By means of the measuring electronics 323, both measuring values of mass flow of the measuring medium through the process receptacle and its concentration of dissolved oxygen may be determined—in particular, simultaneously—based upon the measuring signals provided by the measuring sensors 303, 304. From these measuring values, the measuring electronics 323 may determine the current oxygen load of the measuring medium on site at the measuring point and output it via the display found at the measuring point.

The measuring electronics 323 may furthermore be designed to determine a measuring point status or a status value representing the measuring value quality of the current measuring value. The measuring value quality in an amperometric oxygen sensor is linked to the flow rate of the flowing measuring medium, since the amperometric oxygen sensor uses up dissolved oxygen during operation. This lowers the measuring value quality in case of a low mass flow of the measuring medium. Consequently, a lower warning threshold level may be stored in the measuring electronics for the flow rate measuring value determined by the measuring sensor 304, corresponding to a minimum flow rate. The measuring electronics 323 are further designed to compare current determined flow rate measuring values with the lower threshold values. If a currently developed flow rate measurement value falls below the lower threshold level, the measuring electronics 323 outputs a warning via the display mentioned above and/or to the operating device and/or the cable 322.

Alternatively or additionally, the measuring electronics 323 may output a status value based upon the threshold value comparison, in addition to the measuring value determined from the measuring signal of the oxygen sensor 316. As long as the current flow rate measuring value is higher than the lower warning threshold value, the status value may be an acronym or symbol representing high reliability of the simultaneously determined measuring values for the oxygen. If the current flow rate measuring value is, however, lower than the lower warning threshold value, the status value may be an acronym or symbol representing low reliability of the simultaneously determined measuring values for the oxygen. The status value may also be a warning signal.

In addition to the lower warning threshold level, there may also be a lower alarm threshold level set for the flow rate measuring values and saved in the measuring electronics 323. If the measuring electronics 323 determine that the flow rate has fallen below the alarm threshold level by comparing a current flow rate measuring value with the alarm threshold value, they may output an alarm signal as a status value via the display, the cable 322, or the radio interface 325 to an operating device.

The measuring electronics 323 may furthermore be designed to output the alarm or warning signals generated on the basis of the threshold value comparisons described above to a superordinate data processing unit optionally connected with the measuring electronics 323.

It is furthermore possible to correct the measuring values of the oxygen sensor 316 based upon the flow rate measuring signal generated by the measuring sensor 304 or use them to calculate the measuring values of the oxygen sensor 316. In the simplest case, a correction value may be stored in the measuring electronics 316 that represents the systematic deviation of the measuring values for the oxygen content of the measuring medium at a flow rate that is below the warning threshold level as determined by the oxygen sensor 316, and which is considered by the measuring electronics 323 when determining the measuring values from the measuring signal of the oxygen sensor when the current flow rate measuring value falls below the lower warning threshold value.

The invention claimed is:

1. An in-line measuring device for capturing at least two measurands of a measuring medium flowing through a process receptacle, comprising:
   a first measuring sensor integrated into the process receptacle, the first measuring sensor designed to generate a first measuring signal that is dependent upon a flow measurand of the measuring medium;
   a second measuring sensor integrated into the process receptacle, the second measuring sensor designed to generate a second measuring signal dependent upon an analysis measurand dependent upon the concentration of at least one analyte in the measuring medium; and
   measuring electronics connected with said first measuring sensor and said second measuring sensor, said measuring electronics configured to receive and process the first measuring signal and the second measuring signal,
   wherein the first measuring sensor, the second measuring sensor and the measuring electronics are disposed within a common housing, the housing integrated into a wall of the process receptacle.

2. The in-line measuring device according to claim 1, wherein:
   said measuring electronics being designed to determine a measuring value for the flow measurand or a qualitative flow rate value from said first measuring signal, and to determine a measuring value of the analysis measurand from said second measuring signal.

3. The in-line measuring device according to claim 1, wherein:
   said measuring electronics being designed to determine values that include values derived from both the first measuring signal and the second measuring signal.

4. The in-line measuring device according to claim 1, wherein:
   said measuring electronics being designed to derive a status value from said first or said second measuring signal and to consider this status value when processing the other measuring signal that is not used to derive the status value.

5. The in-line measuring device according to claim 4, wherein:
   said measuring electronics being designed to compare the measuring signal used to derive the status value or a value derived from the measuring signal with at least one reference value to determine the status value.

6. The in-line measuring device according to claim 4, wherein:
   said measuring electronics including a display device; and
   said measuring electronics being designed to output a warning or an alarm on the basis of the determined status value on the display device.

7. The in-line measuring device according to claim 1, further comprising:
   an energy supply unit that is designed to supply both said first and said second measuring sensors and said measuring electronics with energy.

8. The in-line measuring device according to claim 1, wherein:
   said measuring electronics being designed to derive a value of a quantity dependent upon both measuring signals by using said first and said second measuring signals.

9. The in-line measuring device according to claim 8, wherein:
   said derived value being a value for a flow rate relating to an analyte contained in said measuring medium.

10. The in-line measuring device according to claim 8, wherein:
    said derived value being a value for an analyte load that represents the analyte amount passing a point of the process receptacle together with the flowing measuring medium within a given period of time.

11. The in-line measuring device according to claim 1, wherein:
    said first and said second measuring sensors being integrated into a flow-through fitting that may be fluidically connected to the process receptacle, providing a flow path along which at least a part of the measuring medium flowing through the process receptacle flows through said flow-through fitting.

12. The in-line measuring device according to claim 11, wherein:
    said process receptacle being a pipe system, with said flow-through fitting being designed as a pipeline section including flanges or anchor points at opposing ends that serve to connect the flow-through fitting to the pipe system.

13. A method for capturing process variables of a measuring medium contained in a process receptacle with an in-line measuring device, the method comprising:
    providing an in-line measuring device for capturing at least two measurands of a measuring medium flowing through a process receptacle, the measuring device including:
    a first measuring sensor integrated into the process receptacle, the first measuring sensor structured to generate a first measuring signal that is dependent upon a flow measurand of the measuring medium;
    a second measuring sensor integrated into the process receptacle, the second measuring sensor structured to generate a second measuring signal dependent upon an analysis measurand dependent upon the concentration of at least one analyte in the measuring medium; and measuring electronics connected with said first measuring sensor and said second measuring sensor, said measuring electronics configured to receive and process the first measuring signal and the second measuring signal, wherein the first measuring sensor, the second measuring sensor and the measuring electronics are disposed within a common housing, the housing integrated into a wall of the process receptacle; and receiving and processing the first measuring signal and the second measuring signal using the measuring electronics.

14. The method according to claim 13, wherein:
using said measuring electronics to determine a measuring value of the analysis measurand by means of the second measuring signal and to determine a status value assigned to the measuring value of the analysis measurand on the basis of said first measuring signal.

15. The method according to claim 14, wherein:
using said measuring electronics to determine the status value on the basis of a comparison of said first or said second measuring signal or a value derived therefrom with one or several reference values.

16. The method according to claim 15, wherein:
outputting a warning or alarm signal as status value using the measuring electronics.

17. The method according to claim 13, wherein:
using said measuring electronics to determine values of a flow rate relating to the analyte on the basis of said first and said second measuring signals, or determining to determine an analyte amount passing a point of the process receptacle with the flowing measuring medium within a given period of time.

18. The in-line measuring device according to claim 1, wherein the second measuring sensor is one of a conductivity sensor, oxygen sensor, pH sensor, ion-selective electrode for determining an ion concentration, optical sensor, spectrometric sensor or a photometric sensor.

19. An in-line measuring device for capturing at least two measurands of a measuring fluid flowing through a process receptacle, comprising:

a first measuring sensor integrated into the process receptacle, the first measuring sensor structured to generate a first measuring signal that is dependent upon a flow measurand of the measuring medium;

a second measuring sensor integrated into the process receptacle, the second measuring sensor structured to generate a second measuring signal dependent upon an analysis measurand in the measuring medium; and measuring electronics connected with said first measuring sensor and said second measuring sensor, wherein said measuring electronics are configured to receive and process the first measuring signal and the second measuring signal, wherein said measuring electronics are configured to derive a value of a quantity dependent upon both the first and second measuring signals by using said first and second measuring signals.

20. The in-line measuring device according to claim 19, wherein:
said derived value being a value for a flow rate relating to an analyte contained in said measuring medium.

21. The in-line measuring device according to claim 19, wherein:
said derived value being a value for an analyte load that represents the analyte amount within the flowing measuring medium passing a point of the process receptacle within a given period of time.

22. The in-line measuring device according to claim 19, wherein the second measuring sensor is one of a conductivity sensor, oxygen sensor, pH sensor, ion-selective electrode for determining an ion concentration, optical sensor, spectrometric sensor or photometric sensor.

* * * * *